(12) United States Patent
Okamoto et al.

(10) Patent No.: US 10,215,947 B2
(45) Date of Patent: Feb. 26, 2019

(54) FIXING INSTRUMENT AND METAL MESH DEVICE

(71) Applicant: Murata Manufacturing Co., Ltd., Nagaokakyo-shi, Kyoto-fu (JP)

(72) Inventors: Yoshiji Okamoto, Nagaokakyo (JP); Seiji Kamba, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 398 days.

(21) Appl. No.: 14/994,287

(22) Filed: Jan. 13, 2016

(65) Prior Publication Data

US 2016/0124177 A1  May 5, 2016

Related U.S. Application Data

(63) Continuation of application No. PCT/JP2015/068324, filed on Jun. 25, 2015.

(30) Foreign Application Priority Data

Jul. 18, 2014 (JP) ................................. 2014-147686

(51) Int. Cl.
  *G02B 7/00*    (2006.01)
  *F16B 2/06*    (2006.01)
  *G01J 3/44*    (2006.01)
  *G01N 21/3581* (2014.01)
  *G01J 3/02*    (2006.01)

(52) U.S. Cl.
  CPC .................. *G02B 7/00* (2013.01); *F16B 2/06* (2013.01); *G01J 3/0202* (2013.01); *G01J 3/4412* (2013.01); *G01J 3/0229* (2013.01); *G01N 21/3581* (2013.01)

(58) Field of Classification Search
  CPC ............ G01N 21/01; G01N 21/35; G02B 7/00
  USPC .................................. 359/894; 356/326, 329
  See application file for complete search history.

(56) References Cited

U.S. PATENT DOCUMENTS 5,253,280 A   10/1993  Mizuta

FOREIGN PATENT DOCUMENTS

| JP | 4-331349 A | 11/1992 |
| JP | 2000-46702 A | 2/2000 |
| JP | 2005-221317 A | 8/2005 |
| JP | 2011-13029 A | 1/2011 |
| WO | WO 2011/070817 A | 6/2011 |

OTHER PUBLICATIONS

PCT/JP2015/068324 Written Opinion dated Aug. 26, 2015.
International Search Report issued for PCT/JP2015/068324, dated Sep. 8, 2015.

*Primary Examiner* — Audrey Y Chang
(74) *Attorney, Agent, or Firm* — Arent Fox LLP

(57) ABSTRACT

A fixing instrument includes a first frame member (2) and a second frame member (3) that clamp and fix an aperture array structure. At least any of conditions of Expression 1: A1+C>B1 and Expression 2: A2+C>B2 is satisfied where A1 represents a distance between a first reference surface (22*a*) and a first inner peripheral fitting face (21*a*), A2 represents a distance between the first reference surface (22*a*) and a first outer peripheral fitting face (21*b*), B1 represents a distance between a second reference surface (32*a*) and a second inner peripheral fitting face (31*a*), B2 represents a distance between the second reference surface (32*a*) and a second outer peripheral fitting face (31*b*), and C represents a thickness of an outer peripheral section (102) of the aperture array structure.

17 Claims, 10 Drawing Sheets

FIXING INSTRUMENT AND METAL MESH DEVICE

CROSS REFERENCE TO RELATED APPLICATIONS

The present application is a continuation of International application No. PCT/JP2015/068324, filed Jun. 25, 2015, which claims priority to Japanese Patent Application No. 2014-147686, filed Jul. 18, 2014, the entire contents of each of which are incorporated herein by reference.

TECHNICAL FIELD

The present invention relates to a fixing instrument and to a metal mesh device including the fixing instrument and an aperture array.

BACKGROUND ART

Spectrometry has hitherto been used to measure characteristics of a measured object by placing the measured object on an aperture array, applying an electromagnetic wave to the aperture array and analyzing a transmittance spectrum thereof or the like. A specific example of the method is a method for measuring the characteristics of a protein (measuring object) by applying a terahertz wave to a metal mesh (one type of aperture array) to which the protein is attached and analyzing a transmittance spectrum thereof.

In such spectrometry, it is common to increase the frequency of the electromagnetic wave and correspondingly decrease the aperture area of apertures in order to increase measurement sensitivity. This is necessary because of limitations on the use of the aperture array which require that the thickness of the aperture array be substantially equal to or more than the wavelength of the applied electromagnetic wave. In particular, the thickness of an aperture array used when a high-frequency (short-wavelength) electromagnetic wave, such as a terahertz wave, is applied is considerably small. For this reason, when the aperture array is held on a stage of a spectroscope, it is sometimes bent (deflected) or creased which may cause measurement errors.

Regarding this point, International Publication No. 2011/070817 proposes a metal mesh device in which an aperture array is clamped by frame members. Since the aperture array can be held and kept in a tensioned manner in this metal mesh device, the above-described deflection and creasing can be suppressed.

SUMMARY OF INVENTION

Technical Problem

However, in the metal mesh device disclosed in Patent Document 1, fixing of the aperture array with the frame members (which, for example, are formed of resin) is sometimes insufficient due to variations in molding accuracy of the frame members. As a result, creases or deflection occurs on the principal surface of the aperture array which can result in changes in the frequency characteristics of the aperture array causing measurement error. This makes it difficult to perform spectrometric measurement with high accuracy and high reproducibility.

In the prior art frame member for supporting the aperture array, fitting parts (which are typically ring-shaped) often did not have sufficient strength and handleability to prevent bending or creasing of the aperture array. In order to increase the strength and handleability of the fitting parts, flange parts (rim parts) are provided around the fitting parts (fixing parts). In this case, the upper limit of the depth of fitting (embedding) of the frame members is determined by the contact of the flange part of one of the frame members with the flange part of the other frame member. For this reason, when the thickness of the fixing parts of the frame members is insufficient due to variations in molding accuracy, the aperture array cannot be sufficiently fixed (clamped).

In view of the foregoing, an object of the present invention is to provide a fixing instrument that allows spectrometric measurement with high sensitivity and high reproducibility by suppressing the change of the frequency characteristics due to creases and bending of an aperture array, and a metal mesh device including the fixing instrument.

Solution to Problem

The present invention provides a fixing instrument adapted to support an aperture array having a central aperture array section with a plurality of apertures extending through opposite surfaces of the aperture array section, and an outer peripheral section surrounding the aperture array section, the fixing instrument comprising:
first and second frame members adapted to clamp the outer peripheral section of the aperture array so as to support the aperture array section in a plane;
the first frame member having:
  a first cavity in which at least a portion of the aperture array section will be located when the outer peripheral section of the aperture array is clamped by the first and second frame members,
  a frame shaped first fixing part that surrounds at least part of the first cavity; and
  a first flange part which extends around at least part of the first fixing part;
the second frame member having:
  a second cavity in which at least a portion of the aperture array section will be located when the outer peripheral section of the aperture array is clamped by the first and second frame members;
  a frame shaped second fixing part that surrounds at least part of the second cavity; and
  a second flange part which extends around at least part of the second fixing part;
the first flange part of the first frame member and the second flange part of the second frame member having opposed first and second reference surfaces, respectively;
the first fixing part having first inner and outer peripheral fitting faces that oppose second inner and outer peripheral fitting faces of the second fixing part, respectively, with respective portions of the outer peripheral section of the aperture array being located between the first and second outer peripheral fitting faces on the one hand the first and second inner peripheral fitting faces on the other;
the first inner peripheral fitting face extending a distance A1 from the first reference surface as measured in a direction perpendicular to the plane of the aperture array section, the first outer peripheral fitting face extending a distance A2 from the first reference surface as measured in a direction perpendicular to the plane of the aperture array section, the second inner peripheral fitting face extending a distance B1 from the second reference surface as measured in a direction perpendicular to the plane of the aperture array section, the second outer peripheral fitting face extending a distance B2 from the second reference surface as measured in a direction perpendicular to the plane of the aperture array section, the outer peripheral surface of the aperture array having a thickness C as measured in a direction perpendicular to the plane of the aperture array section; and the dimensions of the first and second frame members satisfying at least one of the following conditions:

$A1+C>B1$, and $A2+C>B2$.

The fitting instrument preferably has dimensions in which A2>A1 and B2 >B1 and A1−B1>A2−B2 and is preferably used for spectrometric measurement that measures characteristics of a measuring object by applying an electromagnetic wave to the aperture array structure in a state in which the measuring object is held on the aperture array structure and detecting frequency characteristics of the electromagnetic wave scattered by the aperture array structure. When so used, the thickness of the aperture array section, as measured perpendicular to the plane in which the aperture array section lies, is within a range of one tenth to ten times a wavelength of the electromagnetic wave.

The invention is further directed towards a device, comprising:

an aperture array having a central aperture array section with a plurality of apertures extending through opposite surfaces of the aperture array section, and an outer peripheral section surrounding the aperture array section;

first and second frame members clamping the outer peripheral section of the aperture array so as to support the aperture array section in a plane;

the first frame member having:
 a first cavity in which at least a portion of the aperture array section will be located when the outer peripheral section of the aperture array is clamped by the first and second frame members,
 a frame shaped first fixing part that surrounds at least part of the first cavity; and
 a first flange part which extends around at least part of the first fixing part;

the second frame member having:
 a second cavity in which at least a portion of the aperture array section will be located when the outer peripheral section of the aperture array is clamped by the first and second frame members;
 a frame shaped second fixing part that surrounds at least part of the second cavity; and
 a second flange part which extends around at least part of the second fixing part;

the first flange part of the first frame member and the second flange part of the second frame member having opposed first and second reference surfaces, respectively;

the first fixing part having first inner and outer peripheral fitting faces that oppose second inner and outer peripheral fitting faces of the second fixing part, respectively, with respective portions of the outer peripheral section of the aperture array being located between the first and second outer peripheral fitting faces on the one hand the first and second inner peripheral fitting faces on the other;

the first inner peripheral fitting face extending a distance A1 from the first reference surface as measured in a direction perpendicular to the plane of the aperture array section, the first outer peripheral fitting face extending a distance A2 from the first reference surface as measured in a direction perpendicular to the plane of the aperture array section, the second inner peripheral fitting face extending a distance B1 from the second reference surface as measured in a direction perpendicular to the plane of the aperture array section, the second outer peripheral fitting face extending a distance B2 from the second reference surface as measured in a direction perpendicular to the plane of the aperture array section, the aperture array section having a thickness C as measured in a direction perpendicular to the plane of the aperture array section; and the dimensions of the aperture array and the first and second frame members satisfying at least one of the following conditions:

$A1+C>B1$, and $A2+C>B2$.

It is preferably that A2>A1 and B2>B1 and A1−B1>A2−B2.

The invention further includes a device, comprising:

an aperture array including an aperture array section lying in a first plane and having a plurality of apertures and an outer periphery section surrounding the aperture array section, the outer periphery section having first and second opposed surfaces;

a fixing instrument comprising first and second frames which cooperate to clamp the periphery section of the aperture array and suppress bending and crimping of the aperture array section while leaving at least a portion of the aperture array section exposed;

the first frame having at least first and second clamping faces, the second frame having at least third and fourth clamping faces which oppose the first and second clamping faces, a first portion of the periphery section of the aperture array being located between the first and third clamping faces and a second portion of the periphery section of the aperture array being located between the second and fourth clamping faces;

the first portion of the periphery section of the aperture array being clamped between the first and third clamping faces with the first and third clamping faces pressed against the first and second opposing surfaces of the outer periphery section, respectively; and the second portion of the periphery section of the aperture array not being clamped between the second and fourth clamping faces because no more than one of the second and fourth clamping faces are pressed against the first and section opposing surfaces of the outer periphery section.

The aperture array section lies in a first plane and the first and second clamping faces lie in respective planes which are parallel to the first plane but spaced from one another in a direction perpendicular to the first plane. The third and fourth clamping faces lie in respective planes which are parallel to the first plane but spaced from one another in a direction perpendicular to the first plane. The first, second, third and fourth clamping surfaces all preferably lie in spaced planes in a direction perpendicular to the first plane.

The present invention also relates to a metal mesh device including both the fixing instrument and the aperture array structure described above.

The metal mesh device is used for spectrometric measurement that measures characteristics of a measuring object by applying an electromagnetic wave to the aperture array structure in a state in which the measuring object is held on the aperture array structure and detecting frequency characteristics of the electromagnetic wave scattered by the aperture array structure, and a thickness of the aperture array section is preferably within a range of one tenth to ten times a wavelength of the electromagnetic wave.

Advantageous Effects of Invention

According to the present invention, creasing and bending of the aperture array structure are suppressed making it possible to provide a fixing instrument in which the change of the frequency characteristics is suppressed and which allows spectrometric measurement with high sensitivity and high reproducibility, and a metal mesh device including the fixing instrument.

BRIEF DESCRIPTION OF DRAWINGS

FIG. 7(b) is a schematic cross-sectional view of the fixing instrument according to the fourth embodiment.

DESCRIPTION OF EMBODIMENTS

Figure 1A:
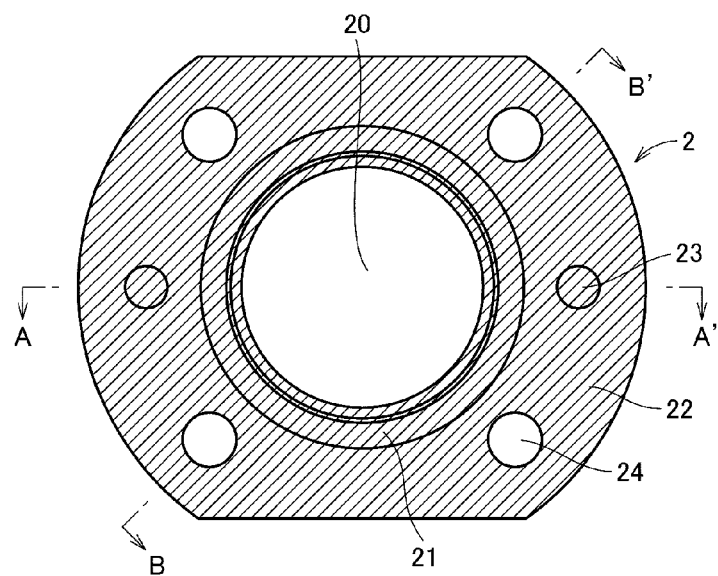
FIG. 1(a) is a plan view of a first frame member forming part of a fixing instrument according to a first embodiment when viewed from a side of a fitting surface thereof.

Embodiments of a fixing instrument and a metal mesh device according to the present invention will be described below with reference to the drawings. In the drawings, the same reference numerals denote the same parts or corresponding parts. The dimensional relationships, such as length, width, thickness and depth, are appropriately changed to clarify and simplify the drawings, but do not show actual dimensional relationships.

<Fixing Instrument>

[First Embodiment]

A fixing instrument according to this embodiment includes a first frame member and a second frame member that clamp and fix an aperture array having a pair of opposed principal surfaces and including an aperture array section in which a plurality of apertures penetrating both of the principal surfaces are arranged and an outer peripheral section provided around the aperture array section. Since details of the aperture array structure will be described later, descriptions thereof are skipped here.

Figure 1B:
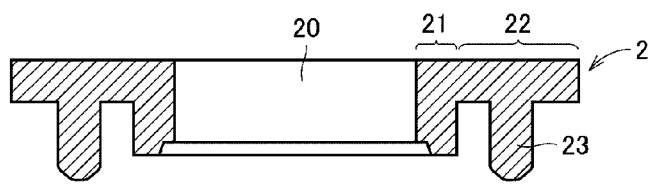
FIG. 1(b) is a schematic cross-sectional view taken along line A-A' of FIG. 1(a).
Figure 1C:
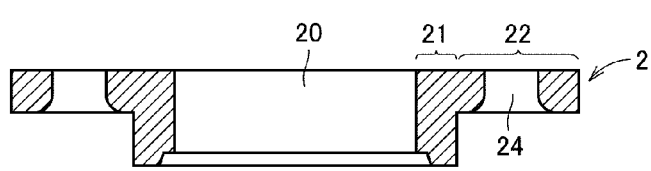
FIG. 1(c) is a schematic cross-sectional view taken along line B-B' of FIG. 1(a).

Referring to FIG. 1(a), a first frame member 2 includes a first cavity 20, a frame-shaped first fixing part 21 surrounding a periphery of the first cavity 20, and a first flange part 22 in contact with an outer periphery of the first fixing part 21. As best shown in FIGS. 1(b) and 1(c), the first flange part 22 has guide members 23 and holes 24.

Figure 2A:
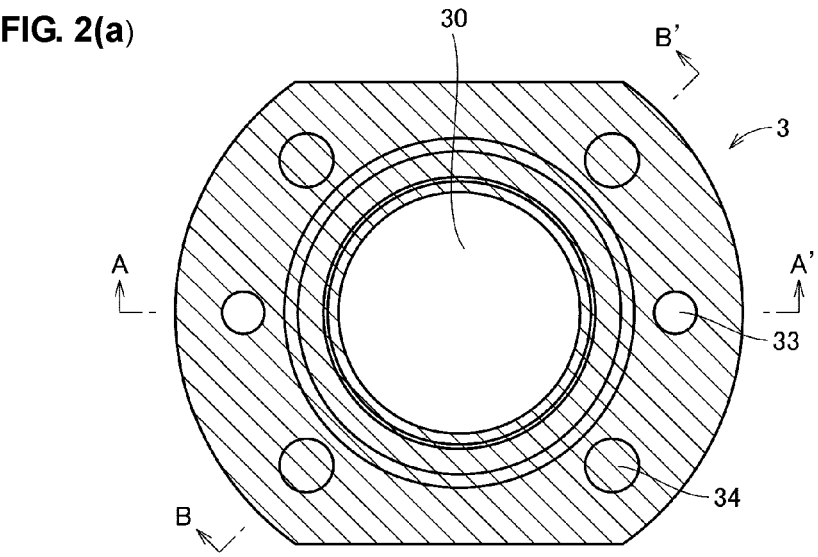
FIG. 2(a) is a plan view of a second frame member viewed from a side of a fitting surface forming part of the fixing instrument according to the first embodiment.
Figure 2B:
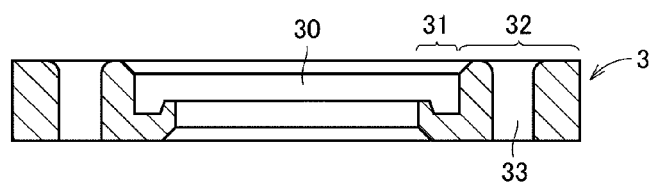
FIG. 2(b) is a schematic cross-sectional view taken along line A-A' of FIG. 2(a).
Figure 2C:
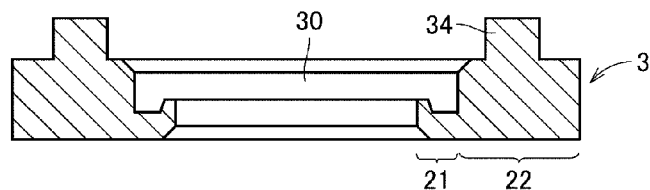
FIG. 2(c) is a schematic cross-sectional view taken along line B-B' of FIG. 2(a).

Referring to FIG. 2, a second frame member 3 includes a second cavity 30, a frame-shaped second fixing part 31 surrounding a periphery of the second cavity 30, and a second flange part 32 in contact with an outer periphery of the second fixing part 31. The second flange part 32 has guide holes 33 (FIGS. 2(a) and 2(b)) and projections 34 (FIGS. 2(a) and 2(c)).

Figure 3:
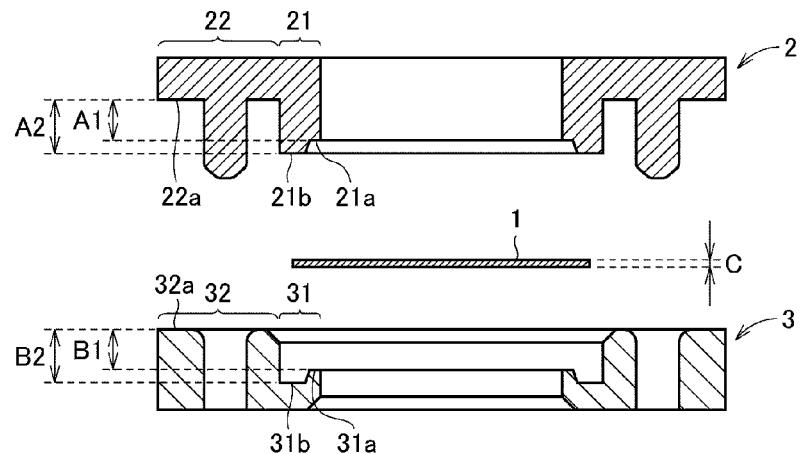
FIG. 3 is a schematic cross-sectional view of a fixing instrument of a first embodiment and an aperture array.

Referring to FIG. 3, an aperture array 1 can be fixed by fitting the first fixing part 21 and the second fixing part 31 with an outer peripheral section of the aperture array 1 being clamped therebetween. In a state in which the aperture array is fixed, the first flange part 22 and the second flange part 32 opposed one another. To clamp the aperture array 1, the guide members 23 (FIG. 1(b)) of the first frame member 2 are fitted in the guide holes 33 (FIG. 2(b)) of the second frame member 3, and the projections 34 (FIGS. 2(a) and 2(c)) of the second frame member 3 are then fitted in the holes 24 (FIGS. 1(a) and 1(c)) of the first frame member 2, so that the aperture array structure 1 is clamped between the first frame member 2 and the second frame member 3.

A fitting surface of the first fixing part 21 projects downwardly with respect to a first reference surface 22a as viewed in FIG. 3 and includes a first inner peripheral fitting face 21a and a first outer peripheral fitting face 21b provided at different distances from the first reference surface 22a.

A fitting surface of the second fixing part 31 is a recessed portion with respect to a second reference surface 32a serving as a surface of the second flange part 32 opposed to the first flange part 22, and includes a second inner peripheral fitting face 31*a* and a second outer peripheral fitting face 31*b* provided at different distances from the second reference surface 32*a*.

Figure 12:
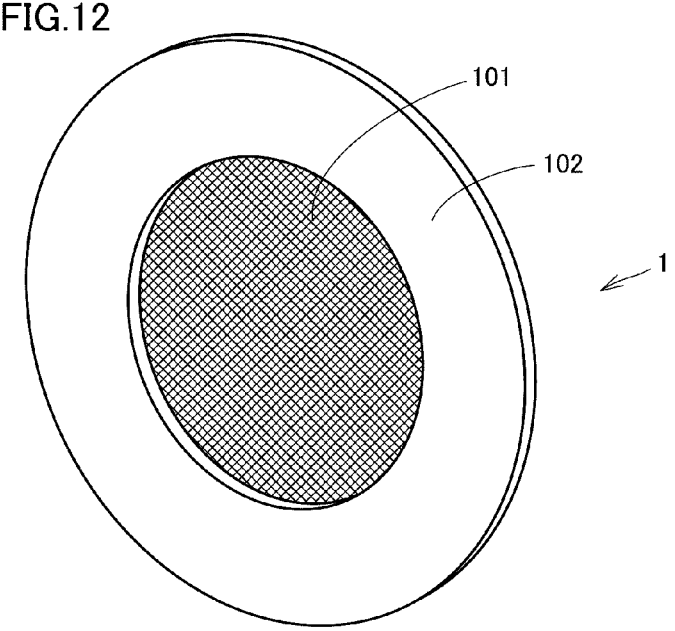
FIG. 12 is a perspective view of an aperture array used in the first embodiment.
Figure 13:
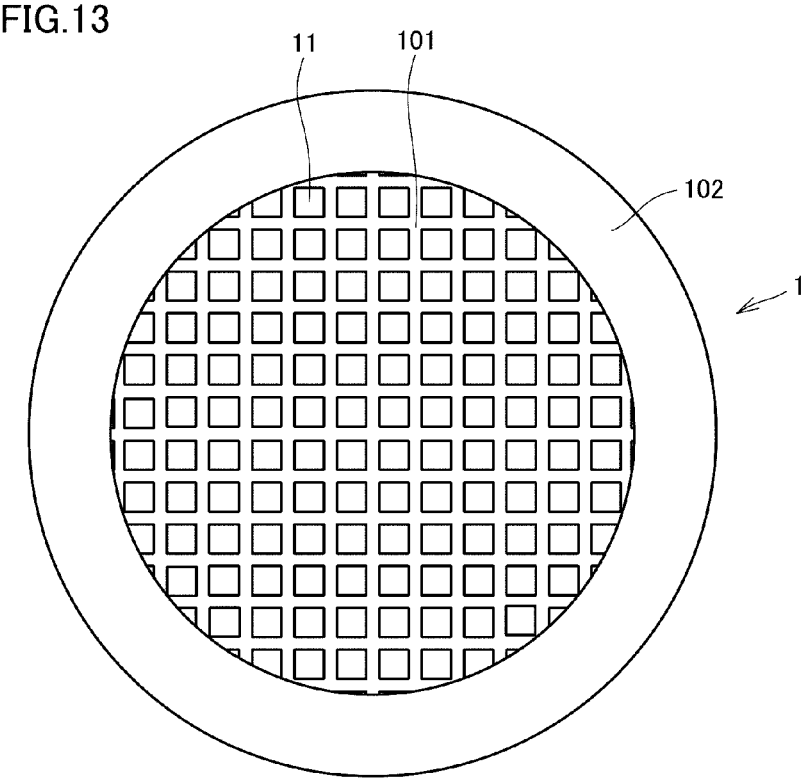
FIG. 13 is a front view illustrating the aperture array used in the first embodiment.

The fixing instrument of this embodiment satisfies at least one of conditions of the following Conditions 1 and 2:

$$A1+C>B1 \quad \text{(Condition 1)}$$

$$A2+C>B2 \quad \text{(Condition 2)}$$

where A1 represents the distance between the first reference surface 22*a* and the first inner peripheral fitting face 21*a*, A2 represents the distance between the first reference surface 22*a* and the first outer peripheral fitting face 21*b*, B1 represents the distance between the second reference surface 32*a* and the second inner peripheral fitting face 31*a*, B2 represents the distance between the second reference surface 32*a* and the second outer peripheral fitting face 31*b*, and C represents the thickness of an outer peripheral section 102 (see FIG. 12) of the aperture array 1.

Figure 15A:
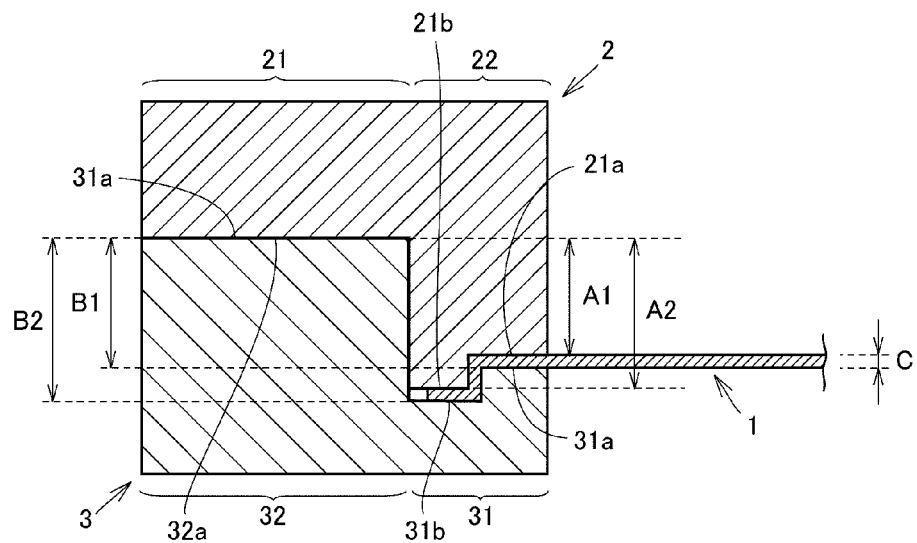
FIGS. 15(a) and (b) are schematic cross-sectional views explaining the dimensional relationship of a fixing instrument of the related art.
Figure 15B:
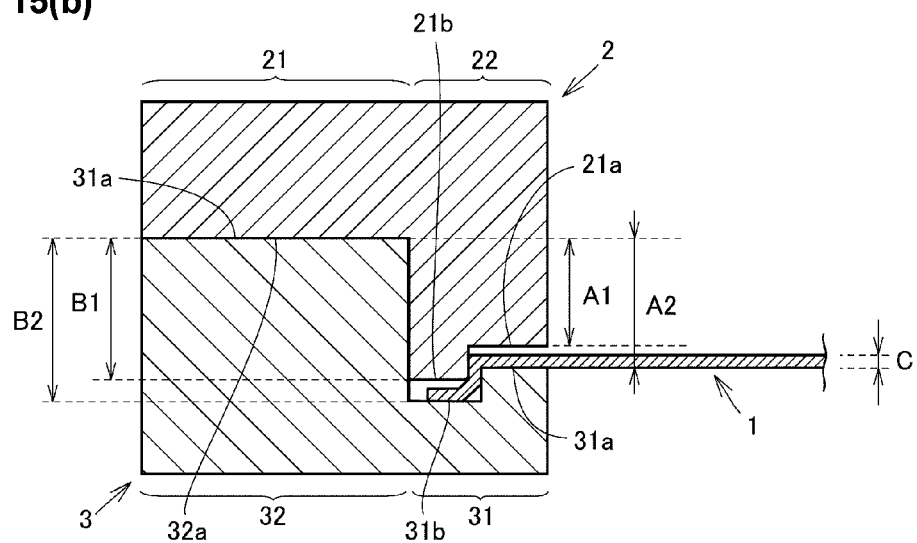

This point will be described in more detail with reference to FIGS. 4(*a*), 4(*b*), 15(*a*) and 15(*b*). FIG. 15(*a*) shows the relationship between the first frame member 2, the second frame member 3 and the aperture array when the frame members are accurately manufactured. In this case the dimensions of the members satisfy the conditions that A1+C=B1 and A2+C=B2. This allows the outer peripheral section of the aperture array 1 to be firmly clamped on the fitting surface sides of the first fixing part 21 of the first frame member 2 and the second fixing part 31 of the second frame member 3. However, in practice it is difficult to consistently manufacture the frame members with this accuracy, for example, when they are made of molded resin. If both the lengths A1 and A2 are less than the designed values or both the lengths B1 and B2 are less than the design values, as illustrated in FIG. 15(*b*), the outer peripheral section of the aperture array 1 is not securely clamped by the first fixing part 21 of the first frame member 2 and the second fixing part 31 of the second frame member 3, and fixing of the aperture array is insufficient.

Figure 4A:
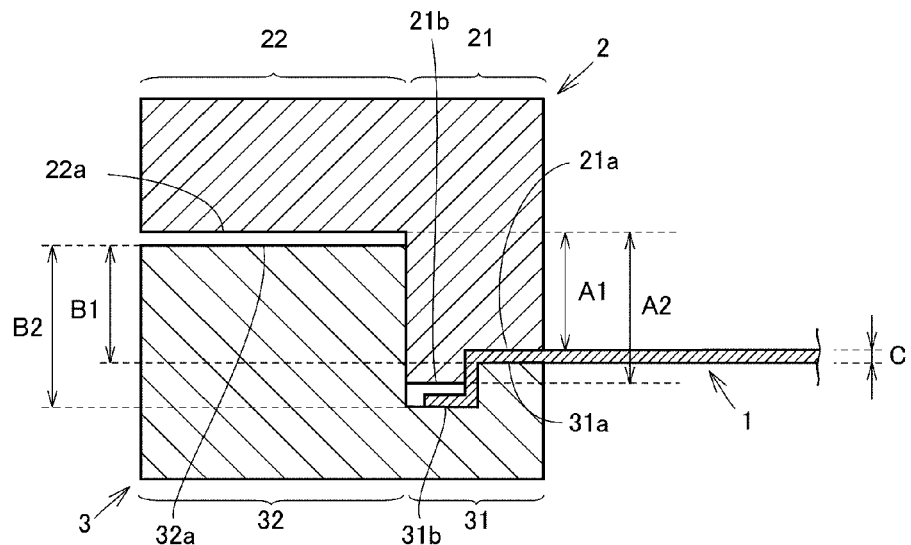
FIGS. 4(a) and 4(b) includes schematic cross-sectional views illustrating the dimensional relationship of the fixing instrument of the first embodiment.
Figure 4B:
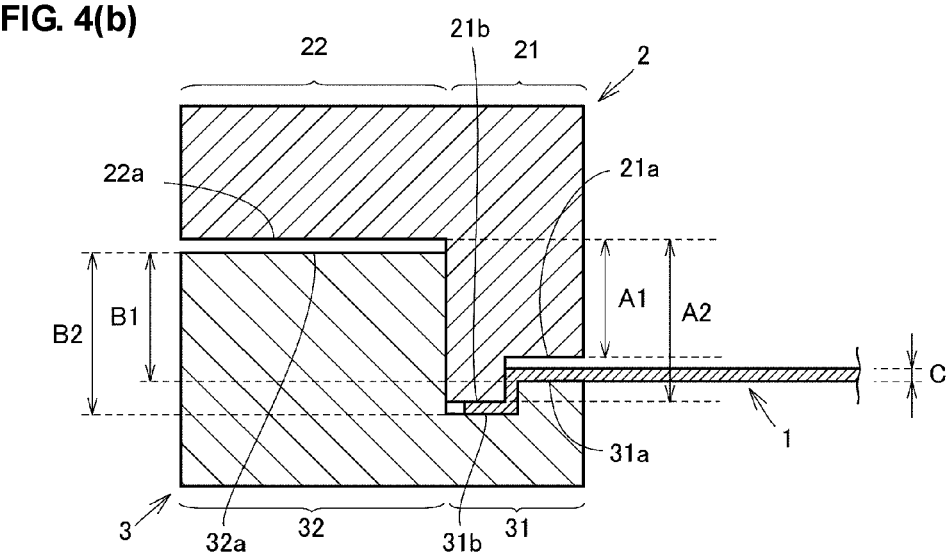

Accordingly, in the fixing member of the first embodiment disclosed herein, the dimensional relationships between A1 and B1 and between A2 and B2, respectively, are designed so that the aperture array 1 can be reliably clamped by the first inner peripheral fitting face 21*a* of the first fixing part 21 and the second inner peripheral fitting face 31*a* of the second fixing part 31, as illustrated in FIG. 4(*a*) or so that the aperture array 1 can be reliably clamped by the first outer peripheral fitting face 21*b* of the first fixing part 21 and the second outer peripheral fitting face 31*b* of the second fixing part 31, as illustrated in FIG. 4(*b*), even when there are variations in molding accuracy of the frame members.

To this end, the dimensions of the frame members used in this embodiment are designed to satisfy at least one of the following conditions shown in FIGS. 4(*a*) and 4(*b*), respectively:

$$A1+C>B1 \quad \text{(Condition 1)}$$

$$A2+C>B2 \quad \text{(Condition 2).}$$

While FIG. 3 illustrates a manner in which A2 is more than A1 and B2 is more than B1, a manner in which A1 is more than A2 and B1 is more than B2 may be adopted as long as at least one of conditions 1 and 2 are satisfied.

By virtue of such dimensional design of the frame members, even when variations in dimensional accuracy of the frame members occur, the aperture array 1 can be reliably fixed. Thus, it is possible to provide a fixing instrument that suppresses the frequency characteristics from being changed by creasing and bending of the aperture array and allows spectrometric measurement with high sensitivity and high reproducibility, and a metal mesh device including the fixing instrument.

However, in order to suppress creasing and bending of the aperture array 1, it is best to reliably clamp the aperture array 1 between the first inner peripheral fitting face 21*a* of the first fixing part 21 and the second inner peripheral fitting face 31*a* of the second fixing part 31, as illustrated in FIG. 4(*a*). Hence, it is preferable to design the dimensions of the frame members so as to satisfy the following Condition 3:

$$A1-B1>A2-B2 \quad \text{(Condition 3).}$$

Thus, the aperture array structure 1 can be fixed more reliably.

While the material of the frame members (first frame member 2 and second frame member 3) is not particularly limited, a resin material, for example, is preferably used from the viewpoints of having little influence on spectrometric measurement and easy working. Examples of resin materials include an engineering plastic material such as polyacetal (POM), polyetheretherketone (PEEK), polyetherimide (PEI), polyphenylenesulfide (PPS), or polyamide (PAI), Teflon (registered trademark), polyethylene, or a polypropylene. When the frame members are molded from such a material whose molding accuracy is apt to vary, such as the resin material, the effects obtained by the present invention are particularly useful.

In the first fixing part 21 of the first frame member 2 and the second fixing part 31 of the second frame member 3, the surfaces (first inner peripheral fitting face 21*a*, first outer peripheral fitting face 21*b*, second inner peripheral fitting face 31*a*, and second outer peripheral fitting face 31*b*) in contact with the outer peripheral section of the aperture array 1 are preferably roughened. Since the surface resistance (frictional coefficient) of the surfaces in contact with the outer peripheral section of the aperture array 1 is increased by roughening, the aperture array 1 can be held more firmly. Further, the aperture array structure can be more reliably held in a tensioned state by the frictional action during fitting.

Figure 8A:
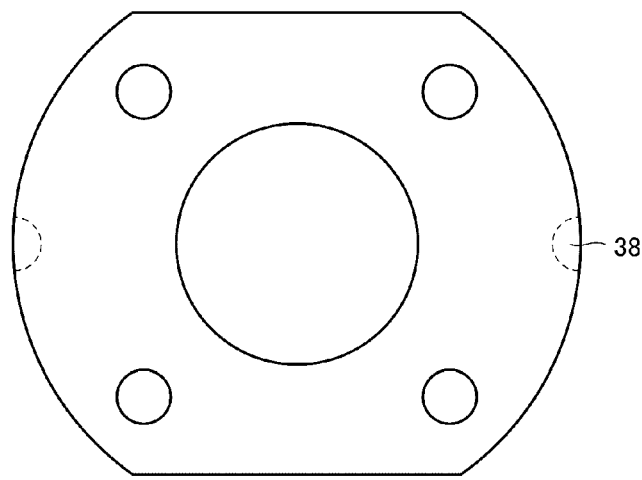
FIG. 8(a) is a top view of a modification of the fixing instrument of the first embodiment.
Figure 8B:
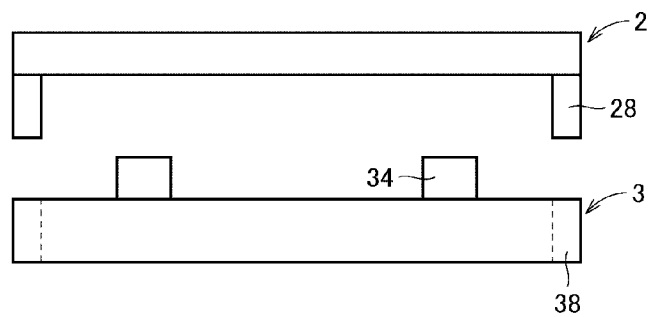
FIG. 8(b) is a schematic cross-sectional view of the fixing instrument according to the modification shown in FIG. 8(a).

Instead of the press-fit guide portions (pins) 23 and the guide holes 33 illustrated in FIGS. 1(*a*) to 3, for example, semicolumnar press-fit guide portions 28 and guide grooves 38 may be provided, as illustrated in FIG. 8.

Figure 9:
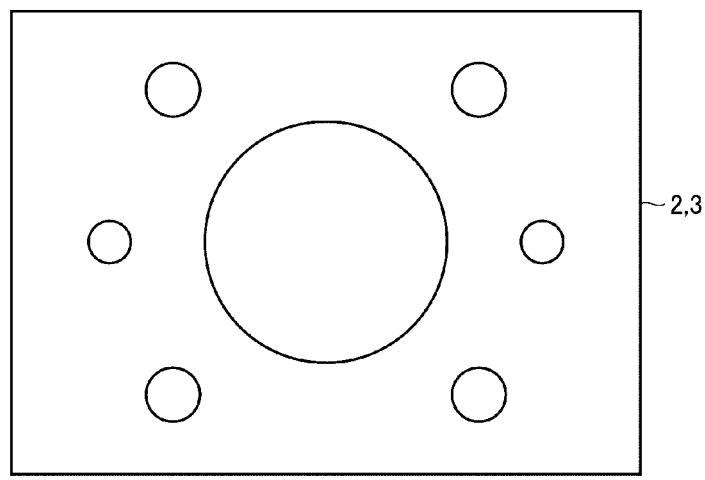
FIG. 9 is a schematic top view illustrating a modification of the overall shape of the fixing instrument of the first embodiment.
Figure 10:
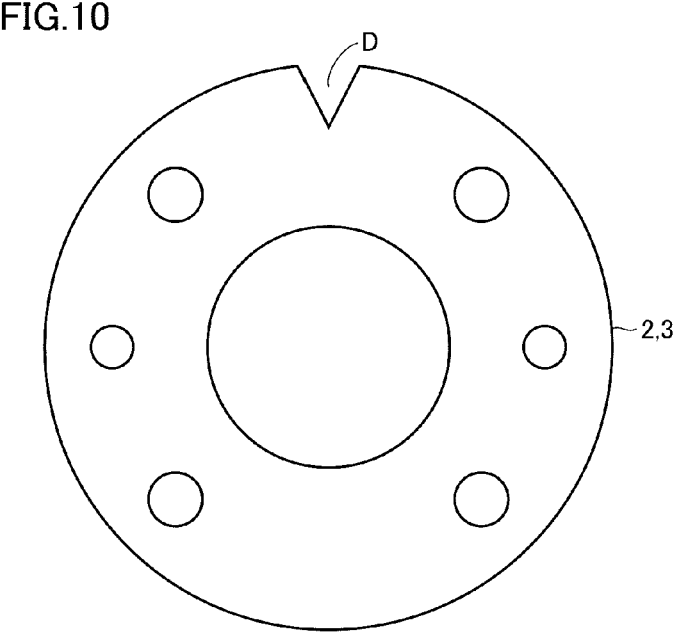
FIG. 10 is a schematic top view illustrating another modification of the overall shape of the fixing instrument of the first embodiment.

The overall shape of the fixing instrument of this embodiment is a disc shape (a circular ring) having opposed D-cuts cut along parallel straight lines. This shape allows the fixing instrument to be more easily positioned in the rotating direction when set in a spectroscope or the like than the disc-shaped fixing instrument. However, the shape of the fixing instrument is not limited to such a shape. For example, a fixing instrument having a rectangular overall shape (first frame member 2 and second frame member 3) illustrated in FIG. 9 or a fixing instrument having a single cutout D as illustrated in FIG. 10, is used, it is still possible to accurately position the fixing instrument when set in the spectroscope or the like.

In the above-described embodiment, the fitting surface side of the first fixing part 21 of the first frame member 2 is composed of the first inner peripheral fitting face 21*a* and the second outer peripheral fitting face 21*b*, and the fitting surface side of the second fixing part 31 of the second frame member 3 is composed of the second inner peripheral fitting face 31a and the second outer peripheral fitting face 31b. That is, while each of the first fixing part 21 and the second fixing part has a pair of fitting faces provided at different distances from the reference surface (first reference surface 22a or second reference surface 32a) in this embodiment, it may have three or more fitting faces provided at different distances from the reference surface. In this case, it is possible to increase the number of times of bending of the aperture array structure 1 when the aperture array structure 1 is clamped, and to more firmly fix the aperture array structure 1.

[Second Embodiment]

Figure 5:
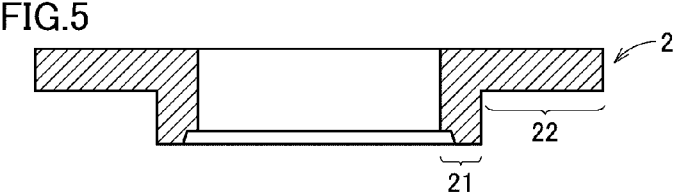
FIG. 5 is a schematic cross-sectional view of a fixing instrument according to a second embodiment.
Figure 5:
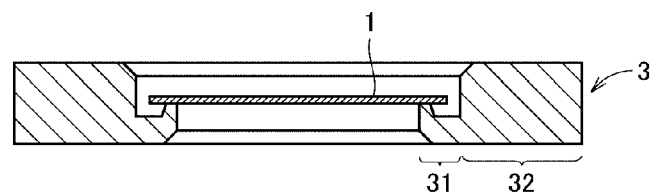

Referring to FIG. 5, a fixing member of this embodiment is different from the first embodiment in that design is made to maintain a fitting state of a first frame member 2 and a second frame member 3 by press-fitting a first fixing part 21 (a projecting portion with respect to a first flange part 22) of the first frame member 2 in a second fixing part 31 (a recessed portion with respect to a second flange part 32) of the second fixing part 31. To that end, the outer diameter of the first fixing part 21 is designed to be slightly larger than the outer diameter of the second fixing part 31 (inner diameter of the second flange part 32). Since the second embodiment is similar to the first embodiment in other respects, redundant descriptions will be skipped.

[Third Embodiment]

Figure 6:
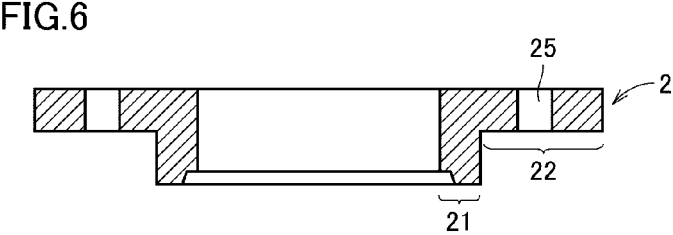
FIG. 6 is a schematic cross-sectional view of a fixing instrument according to a third embodiment.
Figure 6:
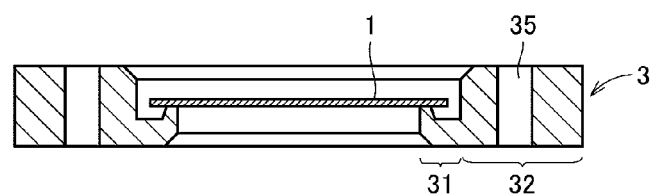

Referring to FIG. 6, a fixing member of this embodiment is different from the first embodiment in that a first flange part 22 of a first frame member 2 has screw holes 25 through which screws pass and a second flange part 32 of a second frame member 3 has screw holes 35 at positions corresponding to the screw holes 25. Since the third embodiment is similar to the first embodiment in other respects, redundant descriptions will be skipped.

[Fourth Embodiment]

Figure 7A:
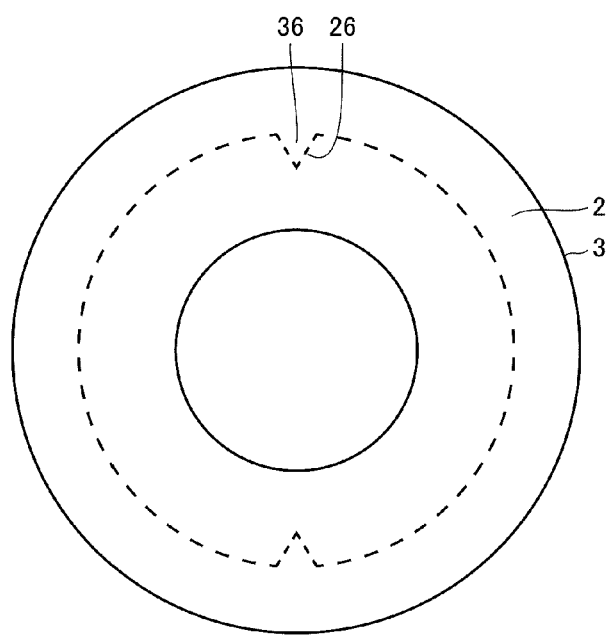
FIGS. 7(a) and 7(b) is a top view of a fixing instrument according to a fourth embodiment.
Figure 7B:
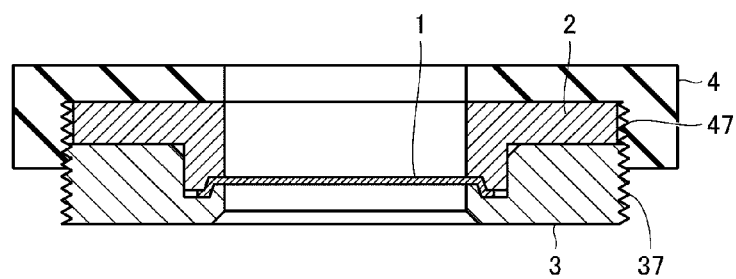

Referring to FIGS. 7(a) and (b), a metal mesh device according to this embodiment is different from the first embodiment in that an aperture array 1 is clamped and fixed between a first frame member 2 and a second frame member 3 by fitting a thread groove 47 on the inner peripheral side of a screw cap 4 and a thread groove 37 on the outer periphery of the second frame member together. To prevent the first frame member 2 from rotating relative to the second frame member 3 when the screw cap 4 is screwed, the first frame member 2 has cutout portions 26, the second frame member 3 has projections 36, and the cutout portions 26 and the projections 36 are fitted together. Since the fourth embodiment is similar to the first embodiment in other respects, redundant descriptions will be skipped.

<Metal Mesh Device>

[Fifth Embodiment]

This embodiment is an embodiment of a metal mesh device according to the present invention. The metal mesh device includes the fixing instrument according to any of the first to fourth embodiments, and an aperture array.

(Aperture Array)

Figure 14A:
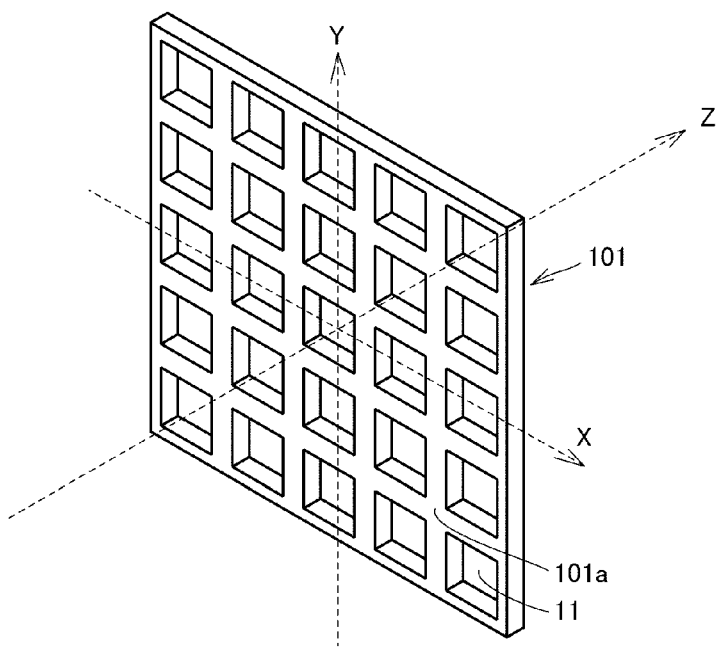
FIG. 14(a) is a perspective view illustrating an aperture array section of the aperture array used in the first embodiment.

As shown in FIGS. 12 through 14(b), the aperture array 1 includes a plurality of apertures 11 perpendicularly penetrating a principal surface 101a (FIG. 14(a)) of the aperture array section 101, and an outer peripheral section 102 surrounding the aperture array section 101. The overall shape of the aperture array 1 is shaped like a disc. A plurality of apertures 11 are arranged over the area of the aperture array section 101 (a disc-shaped portion on the inner peripheral side of the aperture array), and an outer peripheral section 102 surrounds the aperture array section 101 (an annular portion on the outer peripheral side).

In the aperture array section of the aperture array used in this embodiment, for example, a plurality of apertures perpendicularly penetrating the principal surface are periodically arranged in at least one direction on the principal surface. However, the apertures do not have to be periodically arranged all over the aperture array section, and it is only necessary that the apertures be periodically arranged in at least a part of the aperture array section. The aperture array section is preferably formed by a periodic or quasi-periodic structure. The quasi-periodic structure refers to a structure that does not have translational symmetry but maintains the arrangement order. Examples of the quasi-periodic structure include a Fibonacci structure serving as a one-dimensional quasi-periodic structure and a Penrose structure serving as a two-dimensional quasi-periodic structure. The periodic structure refers to a structure having spatial symmetry, as represented by translational symmetry, and is classified into a one-dimensional periodic structure, a two-dimensional periodic structure, and a three-dimensional periodic structure according to the dimension of the symmetry. Examples of the one-dimensional periodic structure include a wire-grid structure and a one-dimensional diffraction grating. Examples of the two-dimensional periodic structure include a mesh filter and a two-dimensional diffraction grating. Among these periodic structures, the two-dimensional periodic structure is suitably used, and a two-dimensional periodic structure in which apertures are regularly arranged in the vertical direction and the horizontal direction (square array) is more suitably used.

An example of a two-dimensional periodic structure in which apertures are arranged in a square is a plate-shaped structure (grating-shaped structure) in which apertures are arranged at regular intervals in a matrix, as illustrated in FIG. 14(a). An aperture array section 101 illustrated in FIG. 14(a) is formed by a plate-shaped structure in which apertures 11 having a square shape as seen from a principal surface 101a side thereof are arranged at equal intervals in two arrangement directions (vertical and lateral directions in FIG. 14(b)) parallel to sides of the square. The shape of the apertures is not limited to a square shape, but may be, for example, a rectangular shape, a circular shape, or an elliptic shape. The intervals do not necessarily need to be equal between the two arrangement directions as long as the square array is achieved, and, for example, a rectangular array may be adopted. Similarly, the overall shapes of the aperture array section and the aperture array structure are not limited.

The shape, dimensions, etc. of the apertures are appropriately designed, for example, in accordance with the measurement method in which the aperture array will be used, the material characteristics of the aperture array (aperture array section and outer peripheral section), and the frequency of the used electromagnetic wave, and it is difficult to generalize the ranges thereof. In the aperture array section 101 illustrated in FIG. 14(a), it is preferable that the grating spaces of the apertures should be larger than the hole size of the apertures as shown in FIG. 14(d) and should preferably be ten times or less the wavelength of the electromagnetic wave used in measurement. While the measurement sensitivity can be generally increased by setting the grating space of the apertures within the range corresponding to the wavelength of the used electromagnetic wave, limitations of working (i.e., the use to which the aperture array will be put) are imposed on the lower limit of the grating space.

Figure 14B:
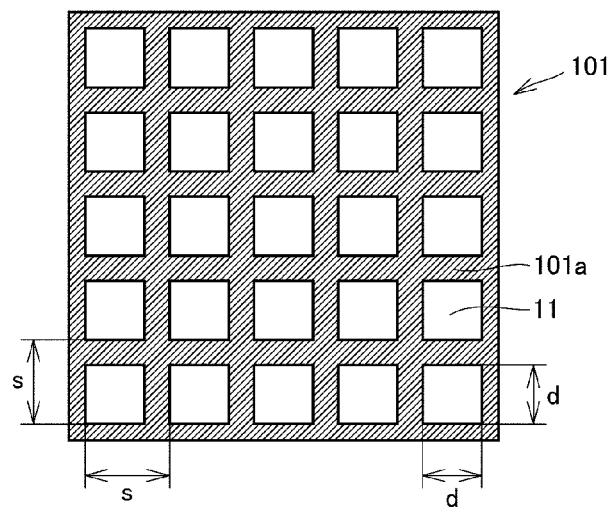
FIG. 14(b) is a schematic view illustrating a grating structure of the aperture array section.

As the hole size of the apertures, the hole size of the apertures shown by d in FIG. 14(b) is preferably one tenth or more the wavelength of the electromagnetic wave used in measurement and smaller than the grating space of the apertures. While the measurement sensitivity can be increased by setting the hole size of the apertures according to the wavelength of the used electromagnetic wave, limitations of working are imposed on the lower limit of the hole size.

The thickness of the aperture array section in the aperture array structure is appropriately designed, for example, in accordance with the measurement method, the material characteristics of the aperture array, and the frequency of the used electromagnetic wave, and it is difficult to generalize the ranges thereof. However, the thickness is preferably within the range of one tenth to ten times the wavelength of the electromagnetic wave used (applied) in measurement. If the thickness of the aperture array section exceeds this range, the intensity of scattering electromagnetic wave decreases, and detection of signals is sometimes difficult. In contrast, if the thickness of the aperture array section falls below this range, a problem with mechanical strength occurs, and the aperture array section is apt to be broken. Hence, it is difficult to use the aperture array section as a self-supported film.

The aperture array is preferably formed of metal. The metal preferably includes non-precious metal, and the aperture array is preferably formed of non-precious metal or an alloy of non-precious metal and other metals. Further, the metal preferably allows a hydroxyl group to be formed on its surface. Examples of such non-precious metal include nickel, stainless steel, titanium, tungsten, iron, chromium, platinum, and gold. The non-precious metal is preferably nickel, stainless steel, titanium, platinum, or gold.

While the overall shape of the aperture array of the preferred embodiment is a disc shape (annular shape), the shape of the aperture array is not limited to such a shape.

For example, when the metal mesh device of this embodiment is set in a spectroscope, it is usually fixed to a metal plate called a stage mounted at a position to be irradiated with an electromagnetic wave. For this reason, when the electromagnetic wave is caused to perpendicularly enter the principal surface of the aperture array structure, for example, design is made so that a surface of the first frame member opposite from the fitting surface is parallel to a surface of the second frame member opposite from the fitting surface. Further, when the electromagnetic wave obliquely enters the aperture array with an incident angle (an angle formed by the traveling direction of the electromagnetic wave and the principal surface of the aperture array), design is made so that the surface of the first frame member opposite from the fitting surface is inclined at a predetermined angle to the surface of the second frame member opposite from the fitting surface. This allows easy preparation for measurement.

While the method for fixing the metal mesh device to the stage of the spectroscope is not particularly limited, for example, a method for fixing the fixing instrument of the metal mesh device to the stage with a press contact member or an adhesive or a method for fixing the fixing instrument of the metal mesh device to the stage by screwing or pin press-fitting can be used. In the latter method, the frame members are provided with holes through which screws or pins are inserted. Alternatively, the metal mesh device may be fixed to the stage by the pressing force utilizing a spring leaf.

(Spectrometric Measurement)

A spectrometric measuring device of the present invention is used for spectrometric measurement. For example, a specific spectrometric measurement method is to measure the characteristics of a measuring object by applying an electromagnetic wave to an aperture array in a state in which the measurement object is held on the aperture array and detecting the frequency characteristics of the electromagnetic wave scattered by the aperture array. First, an example of such spectrometric measurement will be described with reference to FIG. 11.

Figure 11:
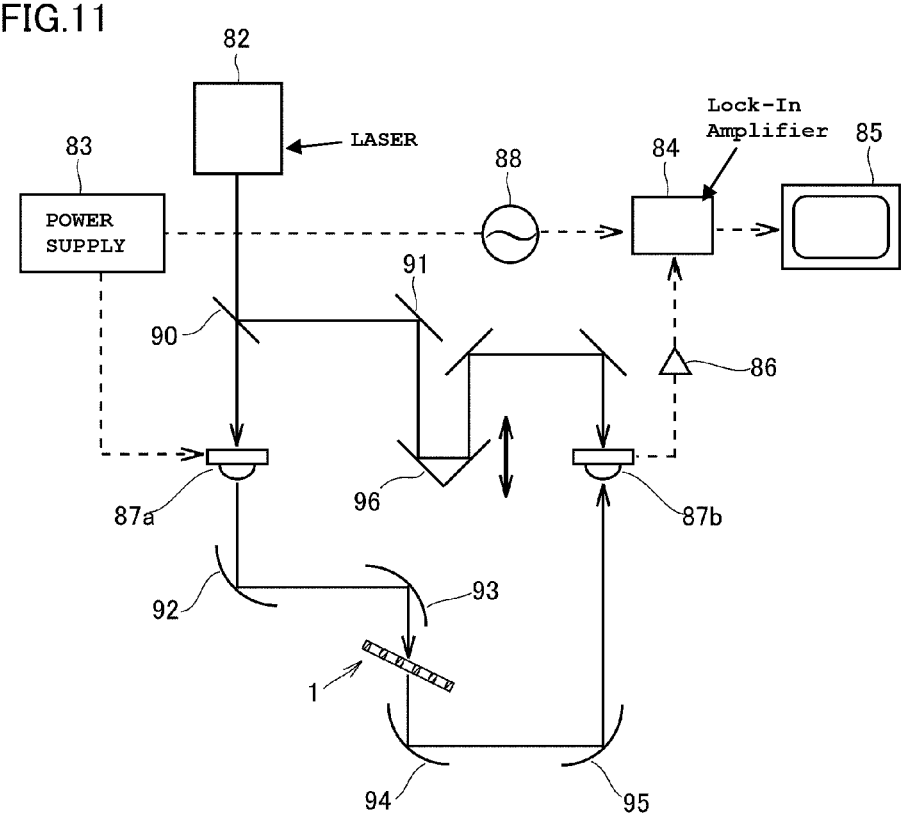
FIG. 11 is a schematic view explaining a measurement example using a metal mesh device according to the present invention.

FIG. 11 is a schematic view illustrating the outline of a detection apparatus used to detect the frequency characteristics in the example of spectrometric measurement. This detection apparatus utilizes an electromagnetic wave pulse generated by applying laser light emitted from a laser 82 onto a semiconductor material.

In the configuration of FIG. 11, laser light emitted from the laser 82 is branched into two parts by a half mirror 90. One part is applied to a photoconductive element 87a on an electromagnetic wave generation side, and the other part is applied to a photoconductive element 87b on a receiving side through a time delay stage 96 by using a plurality of mirrors 91 (reference numerals of mirrors having similar functions are omitted). As each of the photoconductive elements 87a and 87b, a general photoconductive element in which a dipole antenna has a gap portion in LT-GaAs (low-temperature grown GaAs) can be used. As the laser 82, for example, a fiber laser or a laser using a solid, such as titanium sapphire, can be used. Further, the electromagnetic wave may be generated and detected by using the surface of the semiconductor without an antenna, or by using an electrooptical crystal such as a ZnTe crystal. Here, an adequate bias voltage is applied from a power supply 83 to the gap portion of the photoconductive element 87a on the generation side.

The generated electromagnetic wave is converted into a parallel beam by a parabolic mirror 92, and is applied onto an aperture array structure 1 by a parabolic mirror 93. The terahertz wave having passed through the aperture array 1 is received by the photoconductive element 87b via parabolic mirrors 94 and 95. An electromagnetic wave signal received by the photoconductive element 87b is amplified by an amplifier 86 and then acquired as a time waveform by a lock-in amplifier 84. Then, the time waveform is subjected to signal processing, such as Fourier transform, in a PC (personal computer) 85 including calculation means, and then, for example, a transmittance spectrum of the aperture array structure 1 is calculated. To acquire the time waveform in the lock-in amplifier 84, the bias voltage applied from the power supply 83 to the gap of the photoconductive element 87a on the generation side is modulated (with an amplitude of 5 to 30V) by using a signal from an oscillator 88. By performing synchronous detection using the bias voltage, the signal to noise ratio can be increased.

The above-described spectrometric measurement (a detection method for the frequency characteristics) is a method generally called a terahertz time-domain spectroscopy (THz-TDS). Besides THz-TDS, for example, a Fourier transform infrared spectroscopy (FT-IR) may be used.

FIG. 11 illustrates a case in which scattering is transmission, that is, the transmittance of the electromagnetic wave is detected. In the present invention, "scattering" means a broad concept including transmission serving as one mode of forward scattering and reflection serving as one mode of backward scattering, and is preferably transmission or reflection. More preferably, scattering is transmission in a zero-order direction or reflection in the zero-order direction.

In general, when s represents the grating space of the diffraction grating, i represents the incident angle, θ represents the diffraction angle, and λ represents the wavelength, a spectrum diffracted by the diffraction grating can be expressed as follows:

$$s(\sin i - \sin \theta) = n\lambda \quad (1).$$

The zero order in the above "zero-order direction" refers to a case in which n in the above equation (1) is 0. Since s and λ cannot become 0, n is equal to 0 only when sin i−sin θ=0. Therefore, the above-described "zero-order direction" means a direction such that the incident angle and the diffraction angle are equal, that is, such that the traveling direction of the electromagnetic wave does not change.

The electromagnetic wave used in detection of the frequency characteristics is not particularly limited as long as it can cause scattering according to the structure of the aperture array structure. For example, any of a radio wave, an infrared ray, a visible ray, an ultraviolet ray, an X-ray, and a gamma ray can be used. While the frequency of the electromagnetic wave is also not particularly limited. The electromagnetic wave is preferably an electromagnetic wave having a frequency of 1 GHz to 1 PHz, more preferably an electromagnetic wave having a frequency of 20 GHz to 240 THz (terahertz wave), and further preferably an electromagnetic wave having a frequency of 20 to 240 THz. While the measurement sensitivity can be generally improved by increasing the frequency of the used electromagnetic wave, it is correspondingly necessary to reduce the size of the apertures. Hence, limitations of working are imposed on the upper limit of the frequency of the electromagnetic wave.

As the electromagnetic wave, for example, a linearly polarized electromagnetic wave (a linearly polarized wave) having a predetermined polarization direction or an unpolarized electromagnetic wave (an unpolarized wave) can be used.

Examples of the linearly polarized electromagnetic wave include a terahertz wave generated by an optical rectification effect of an electrooptical crystal, such as ZnTe, by using a short pulse laser as a light source, visible light emitted from a semiconductor laser, and an electromagnetic wave radiated from a photoconductive antenna. An example of the unpolarized electromagnetic wave is infrared light radiated from a high-pressure mercury lamp or a ceramic lamp.

The metal mesh device of the present invention can also be applied to collect an object in fluid by filtering the object. When the metal mesh device is applied to such filtration, if it is creased or bent, the size of the apertures is sometimes decreased. As a result, a substance that should be originally transmitted is sometimes collected. Further, if the metal mesh has creases or deflection, the strength of the metal mesh decreases when transmitting the fluid, and the metal mesh is sometimes broken or destroyed. In contrast, since the metal mesh device of the present invention can suppress creases and deflection, it can avoid trouble when used for filtration.

The embodiments disclosed herein are illustrative in all respects, and should be considered as not restrictive. The scope of the present invention is shown not by the above description but by the scope of the claims, and it is intended to include all modifications within the meaning and scope equivalent to the scope of claims.

The invention claimed is:

1. A fixing instrument adapted to support an aperture array having a central aperture array section with a plurality of apertures extending through opposite surfaces of the aperture array section, and an outer peripheral section surrounding the aperture array section, the fixing instrument, comprising:

first and second frame members adapted to clamp the outer peripheral section of the aperture array so as to support the aperture array section in a plane;

the first frame member having:
 a first cavity in which at least a portion of the aperture array section will be located when the outer peripheral section of the aperture array is clamped by the first and second frame members;
 a frame shaped first fixing part that surrounds at least part of the first cavity; and
 a first flange part which extends around at least part of the first fixing part;

the second frame member having:
 a second cavity in which at least a portion of the aperture array section will be located when the outer peripheral section of the aperture array is clamped by the first and second frame members:
 a frame shaped second fixing part that surrounds at least part of the second cavity; and
 a second flange part which extends around at least part of the second fixing part;

the first flange part of the first frame member and the second flange part of the second frame member having opposed first and second reference surfaces, respectively;

the first fixing part having first inner and outer peripheral fitting faces that oppose second inner and outer peripheral fitting faces of the second fixing part, respectively, with respective portions of the outer peripheral section of the aperture array being located between the first and second outer peripheral fitting faces on the one hand and the first and second inner peripheral fitting faces on the other;

the first inner peripheral fitting face extending a distance A1 from the first reference surface as measured in a direction perpendicular to the plane of the aperture array section, the first outer peripheral fitting face extending a distance A2 from the first reference surface as measured in a direction perpendicular to the plane of the aperture array section, the second inner peripheral fitting face extending a distance B1 from the second reference surface as measured in a direction perpendicular to the plane of the aperture array section, the second outer peripheral fitting face extending a distance B2 from the second reference surface as measured in a direction perpendicular to the plane of the aperture array section, the outer peripheral surface of the aperture array having a thickness C as measured in a direction perpendicular to the plane of the aperture array section; and the dimensions of the first and second frame members satisfying at least one of the following conditions:

$A1+C>B1$, and $A2+C>B2$.

2. The fixing instrument of claim 1, wherein A2>A1 and B2>B1.

3. The fixing instrument according to claim 1, wherein A1−B1>A2−B2.

4. A device, comprising:

an aperture array having a central aperture array section with a plurality of apertures extending through opposite surfaces of the aperture array section, and an outer peripheral section surrounding the aperture array section;

first and second frame members clamping the outer peripheral section of the aperture array so as to support the aperture array section in a plane;

the first frame member having:
- a first cavity in which at least a portion of the aperture array section will be located when the outer peripheral section of the aperture array is clamped by the first and second frame members,
- a frame shaped first fixing part that surrounds at least part of the first cavity; and
- a first flange part which extends around at least part of the first fixing part;

the second frame member having:
- a second cavity in which at least a portion of the aperture array section will be located when the outer peripheral section of the aperture array is clamped by the first and second frame members;
- a frame shaped second fixing part that surrounds at least part of the second cavity; and
- a second flange part which extends around at least part of the second fixing part;

the first flange part of the first frame member and the second flange part of the second frame member having opposed first and second reference surfaces, respectively;

the first fixing part having first inner and outer peripheral fitting faces that oppose second inner and outer peripheral fitting faces of the second fixing part, respectively, with respective portions of the outer peripheral section of the aperture array being located between the first and second outer peripheral fitting faces on the one hand and the first and second inner peripheral fitting faces on the other;

the first inner peripheral fitting face extending a distance $A1$ from the first reference surface as measured in a direction perpendicular to the plane of the aperture array section, the first outer peripheral fitting face extending a distance $A2$ from the first reference surface as measured in a direction perpendicular to the plane of the aperture array section, the second inner peripheral fitting face extending a distance $B1$ from the second reference surface as measured in a direction perpendicular to the plane of the aperture array section, the second outer peripheral fitting face extending a distance $B2$ from the second reference surface as measured in a direction perpendicular to the plane of the aperture array section, the aperture array section having a thickness $C$ as measured in a direction perpendicular to the plane of the aperture array section; and the dimensions of the aperture array and the first and second frame members satisfying at least one of the following conditions:

$$A1+C>B1, \text{ and}$$

$$A2+C>B2.$$

5. The device of claim 4, wherein $A2>A1$ and $B2>B1$.

6. The device of claim 4, wherein $A1-B1>A2-B2$.

7. The device of claim 4, wherein:
the device is used for spectrometric measurement that measures characteristics of a measuring object by applying an electromagnetic wave to the aperture array structure in a state in which the measuring object is held on the aperture array structure and detecting frequency characteristics of the electromagnetic wave scattered by the aperture array structure, and a thickness of the aperture array section is within a range of one tenth to ten times a wavelength of the electromagnetic wave.

8. A device, comprising:
an aperture array having a center and including an aperture array section lying in a first plane and having a plurality of apertures and an outer periphery section surrounding the aperture array section, the outer periphery section having first and second opposed surfaces;

first and second frames which cooperate to clamp the outer periphery section of the aperture array and suppress bending and crimping of the aperture array section while leaving at least a portion of the aperture array section exposed;

the first frame including first, second, third, fourth and fifth faces which, when viewed along a second plane running perpendicular to the first plane, are located such that the first face is closer to the center of the aperture array than the second, third, fourth and fifth faces, the second face is closer to the center of the aperture array than the third, fourth and fifth faces, the third face is closer to the center of the aperture array than the fourth and fifth faces, and the fourth face is closer to the center of the aperture array than the fifth face, the first, second and third faces defining a first step with the second face extending between the first and third faces, the third, fourth and fifth faces defining a second step with the fourth face extending between the third and fifth faces;

the second frame including sixth, seventh, eighth, ninth and tenth faces which, when viewed along the second plane, are located such that the sixth face is closer to the center of the aperture array than the seventh, eighth, ninth and tenth faces, the seventh face is closer to the center of the aperture array than the eighth, ninth and tenth faces, the eighth face is closer to the center of the aperture array than the ninth and tenth faces and the ninth face is closer to the center of the aperture array than the tenth face, the sixth, seventh and eighth faces defining a third step with the seventh face extending between the sixth and eighth faces, and the eighth, ninth and tenth faces defining a fourth step with the ninth face extending between the eighth and tenth faces;

the first and sixth faces opposing one another with a first portion of the outer periphery section of the aperture array located there between;

the second and seventh faces opposing one another with a second portion of the outer periphery section of the aperture array located there between;

the third and eighth faces opposing one another with a third portion of the outer periphery section of the aperture array located there between, the first and second opposed surfaces of the second portion of the outer periphery section of the aperture array contacting the second and seventh faces, respectively;

the fourth and ninth faces opposing one another without any portion of the outer periphery section of the aperture array located there between; and the fifth and tenth faces opposing one another without any portion of the outer periphery section of the aperture array located there between.

9. The device of claim 8, wherein the aperture array is made of metal.

10. The device of claim 8, wherein the first and third faces lie in respective planes which are parallel to the first plane but spaced from one another in a direction perpendicular to the first plane.

11. The device of claim 10, wherein the fifth and tenth faces lie in respective planes which are parallel to the first plane but spaced from one another in a direction perpendicular to the first plane.

12. The device of claim 11, wherein the second and seventh faces lie in respective planes which are perpendicular to the first plane.

13. The device of claim 8, wherein the second and seventh faces lie respective planes that are slanted relative to the first plane.

14. The device of claim 8, wherein the second and seventh faces lie in respective planes which are slanted with respect to the first plane.

15. The device of claim 8, wherein the first, third, fifth, sixth, eighth and tenth surfaces lie in respective planes which are parallel to the first plane.

16. The device of claim 15, wherein the second, fourth, seventh and ninth surfaces lie in respective planes that are perpendicular to the first plane.

17. The device of claim 8, wherein the fourth and ninth surfaces lie in respective planes that are perpendicular to the first plane and the second and seventh surfaces lies in respective planes that are slanted with respect to the first plane.

* * * * *